United States Patent
Schuldt-Hempe et al.

(10) Patent No.: US 7,156,858 B2
(45) Date of Patent: Jan. 2, 2007

(54) IMPLANT

(75) Inventors: Barbara Schuldt-Hempe, Bad (DE); Christoph Walther, Kattendorf (DE)

(73) Assignee: Ethicon G.m.b.H. (DE)

( * ) Notice: Subject to any disclaimer, the term of this patent is extended or adjusted under 35 U.S.C. 154(b) by 363 days.

(21) Appl. No.: 10/257,432

(22) PCT Filed: Feb. 21, 2001

(86) PCT No.: PCT/EP01/01977

§ 371 (c)(1),
(2), (4) Date: Oct. 10, 2002

(87) PCT Pub. No.: WO01/80773

PCT Pub. Date: Nov. 1, 2001

(65) Prior Publication Data

US 2003/0100954 A1   May 29, 2003

(30) Foreign Application Priority Data

Apr. 20, 2000 (DE) ................................ 100 19 604

(51) Int. Cl.
A61B 17/04 (2006.01)
(52) U.S. Cl. ..................................... 606/151
(58) Field of Classification Search ................. 606/151
See application file for complete search history.

(56) References Cited

U.S. PATENT DOCUMENTS

| | | |
|---|---|---|
| 3,182,662 A | 5/1965 | Shirodkar |
| 3,212,502 A | 10/1965 | Myers |
| 3,311,110 A | 3/1967 | Singrman |
| 3,372,695 A | 3/1968 | Beliveau et al. |
| 3,472,232 A | 10/1969 | Earl |
| 3,608,095 A | 9/1971 | Barry |
| 3,763,860 A | 10/1973 | Clarke |
| 3,858,783 A | 1/1975 | Kapitanov et al. |
| 3,924,633 A | 12/1975 | Cook et al. |
| 4,037,603 A | 7/1977 | Wendorff |
| 4,128,100 A | 12/1978 | Wendorff |
| 4,235,238 A | 11/1980 | Ogiu et al. |
| 4,392,495 A | 7/1983 | Bayers |
| 4,441,497 A | 4/1984 | Paudler |
| 4,509,516 A | 4/1985 | Richmond |
| 4,549,545 A | 10/1985 | Levy |
| 4,655,221 A | 4/1987 | Devereux |
| 4,854,316 A * | 8/1989 | Davis .......................... 606/153 |
| 4,946,467 A | 8/1990 | Ohi et al. |
| 5,013,292 A | 5/1991 | Lemay |

(Continued)

FOREIGN PATENT DOCUMENTS

AU          278089 B     6/1965

(Continued)

OTHER PUBLICATIONS

"Mesh For Pelvic Floor Repair" U.S. Appl. No. 10/263,933, filed Oct. 3, 2002.

(Continued)

Primary Examiner—Michael J. Hayes

(57) ABSTRACT

An implant (1) has an areal basic structure made from weft-knitted or warp-knitted fabric which has a greater extendability in a central area (3) than in the peripheral area (4) of the implant (1). The basic structure can be deformed in the central area (3) of the implant (1) to produce a projection (30) into the third dimension. The implant (1) preferably has a stiffening structure (22, 24) in the area of the free end (32) of the projection (30). The implant (1) is particularly suitable for treating hernias.

9 Claims, 7 Drawing Sheets

U.S. PATENT DOCUMENTS

Figure 1:
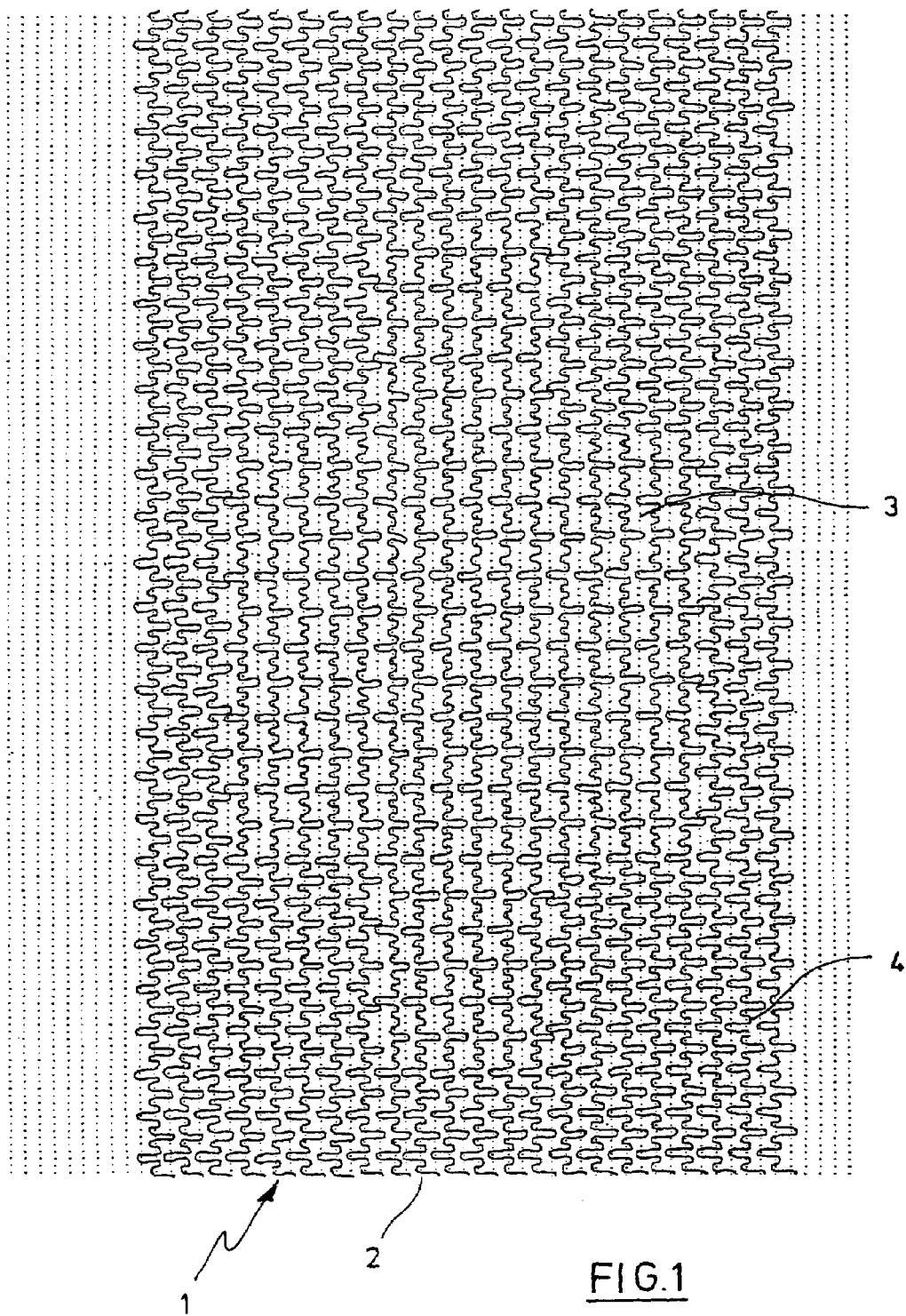

| | | | |
|---|---|---|---|
| 5,032,508 A | | 7/1991 | Naughton et al. |
| 5,080,667 A | | 1/1992 | Chen et al. |
| 5,112,344 A | | 5/1992 | Petros |
| 5,180,385 A | | 1/1993 | Sontag |
| 5,250,033 A | | 10/1993 | Evans et al. |
| 5,254,133 A | * | 10/1993 | Seid ............................ 606/215 |
| 5,281,237 A | | 1/1994 | Gimpelson |
| 5,337,736 A | | 8/1994 | Reddy |
| 5,362,294 A | | 11/1994 | Seitzinger |
| 5,368,595 A | | 11/1994 | Lewis |
| 5,368,756 A | | 11/1994 | Vogel et al. |
| 5,382,257 A | | 1/1995 | Lewis et al. |
| 5,383,904 A | | 1/1995 | Totakura et al. |
| 5,403,328 A | | 4/1995 | Shallman |
| 5,450,860 A | | 9/1995 | O'Connor |
| 5,480,436 A | | 1/1996 | Bakker et al. |
| 5,507,796 A | | 4/1996 | Hasson |
| 5,582,188 A | | 12/1996 | Benderev |
| 5,611,515 A | | 3/1997 | Benderev et al. |
| 5,628,756 A | | 5/1997 | Barker, Jr. et al. |
| 5,645,568 A | | 7/1997 | Chervitz et al. |
| 5,686,090 A | | 11/1997 | Schilder et al. |
| 5,725,577 A | * | 3/1998 | Saxon ...................... 623/23.72 |
| 5,741,299 A | | 4/1998 | Rudt |
| 5,743,917 A | | 4/1998 | Saxon |
| 5,813,975 A | * | 9/1998 | Valenti .......................... 600/37 |
| 5,816,258 A | | 10/1998 | Jervis |
| 5,836,315 A | | 11/1998 | Benderev et al. |
| 5,840,011 A | | 11/1998 | Landgrebe et al. |
| 5,855,549 A | | 1/1999 | Newman |
| 5,860,425 A | | 1/1999 | Benderev et al. |
| 5,899,909 A | | 5/1999 | Claren et al. |
| 5,899,999 A | | 5/1999 | De Bonet |
| 5,922,026 A | * | 7/1999 | Chin ........................ 623/23.72 |
| 5,934,283 A | | 8/1999 | Willem et al. |
| 5,935,122 A | | 8/1999 | Fourkas et al. |
| 5,945,122 A | | 8/1999 | Abra et al. |
| 5,990,379 A | * | 11/1999 | Gregory ...................... 128/898 |
| 5,997,554 A | | 12/1999 | Thompson |
| 6,030,393 A | | 2/2000 | Corlew |
| 6,042,534 A | | 3/2000 | Gellman et al. |
| 6,090,116 A | * | 7/2000 | D'Aversa et al. ........... 606/151 |
| 6,110,101 A | | 8/2000 | Tihon et al. |
| 6,113,641 A | * | 9/2000 | Leroy et al. ............. 623/23.75 |
| 6,117,067 A | | 9/2000 | Gil-Vernet |
| 6,162,537 A | * | 12/2000 | Martin et al. ................ 428/373 |
| 6,197,036 B1 | | 3/2001 | Tripp et al. |
| 6,221,005 B1 | | 4/2001 | Bruckner et al. |
| 6,267,772 B1 | * | 7/2001 | Mulhauser et al. ......... 606/151 |
| 6,273,852 B1 | | 8/2001 | Lehe et al. |
| 6,306,079 B1 | | 10/2001 | Trabucco |
| 6,334,446 B1 | | 1/2002 | Beyar |
| 6,382,214 B1 | | 5/2002 | Raz et al. |
| 6,406,423 B1 | | 6/2002 | Scetbon |
| 6,436,030 B1 | * | 8/2002 | Rehil .......................... 600/37 |
| 6,475,139 B1 | | 11/2002 | Miller |
| 6,491,703 B1 | | 12/2002 | Ulmsten |
| 6,605,097 B1 | | 8/2003 | Lehe et al. |
| 6,610,006 B1 | * | 8/2003 | Amid et al. .................. 600/37 |
| 2001/0018549 A1 | | 8/2001 | Scetbon |
| 2001/0049467 A1 | | 12/2001 | Lehe et al. |
| 2002/0028980 A1 | | 3/2002 | Thierfelder et al. |
| 2002/0058959 A1 | | 5/2002 | Gellman |
| 2002/0077526 A1 | | 6/2002 | Kammerer et al. |
| 2002/0091373 A1 | | 7/2002 | Berger |
| 2002/0188169 A1 | | 12/2002 | Kammerer et al. |
| 2003/0023138 A1 | | 1/2003 | Luscombe |
| 2003/0149440 A1 | | 8/2003 | Kammerer et al. |
| 2003/0176762 A1 | | 9/2003 | Kammerer et al. |

FOREIGN PATENT DOCUMENTS

| | | |
|---|---|---|
| AU | 441561 B | 1/1972 |
| DE | 4220283 A1 | 12/1993 |
| DE | 4334419 A1 | 4/1995 |
| EP | 0598976 A2 | 6/1994 |
| EP | 0774240 A1 | 5/1997 |
| EP | 0 888 756 A | 1/1999 |
| EP | 0941712 A1 | 9/1999 |
| EP | 1025811 A2 | 8/2000 |
| FR | 2 735 015 A | 12/1996 |
| FR | 2 769 825 A | 4/1999 |
| SE | 503271 | 4/1996 |
| WO | WO 9003766 A1 | 4/1990 |
| WO | WO 92/13500 A1 | 8/1992 |
| WO | WO 92/19162 A2 | 11/1992 |
| WO | WO 9606567 A1 | 3/1996 |
| WO | WO 9713465 A1 | 4/1997 |
| WO | WO 9831301 A1 | 7/1998 |
| WO | WO 01/06951 A1 | 2/2001 |
| WO | WO 01/39670 A1 | 6/2001 |
| WO | WO 02/28312 A1 | 4/2002 |
| WO | WO 0238079 A2 | 5/2002 |
| WO | WO 02078568 A1 | 10/2002 |
| WO | WO 04/012626 A1 | 2/2004 |

OTHER PUBLICATIONS

"Mesh Tape With Wing-Like Extensions For Treating Female Urinary Incontinence", U.S. Appl. No. 10/854,289, filed May 7, 2004.

Petros, P.E. Papa, "Vault Prolapse II: Restoration of Dynamic Vaginal Supports by Infracoccygeal Sacropexy, an Axial Day-Case Vaginal Procedure", International Urogynecol Journal, Springer-Verlag London Ltd., 2001, vol. 12, p. 263-303.

Petros, P.E. Papa, "Vault Prolapse 1: Dynamic Supports of the Vagina", International Urogynecol Journal, Springer-Verlag London Ltd., 2001, vol. 12, pp. 292-295.

Petros, P.E. Papa, "An Integral Theory for the Diagnosis and Management of Female Urinary Incontinence", Scandinavian Journal of Urology and Nephrology, Supplement 153: 1993.

"TVT Tension-Free Vaginal Tape, Minimally Invasive Highly Effective Treatment for Female Stress Urinary Incontinence", Gynecare, Ethicon, Inc., 1999, pp. 1-6.

Giberti, "Transvaginal Sacrospinous Colpopexy by Palpation-A New Minimally Invasive Procedure Using An Anchoring System", Urology, (2001) pp. 666-668, vol. 57.

Cosson et al., "Cystocele Repair by Vaginal Patch", Progres En Urologie (2001) pp. 340-346, vol. 11.

Collinet et al., "The Vaginal Patch for Vaginal Cure of Cystocele", J. Gynecol. Obstet. Biol. Reprod. No. 2 (2000) pp. 197-201, vol. 29.

Leanza et al., "New Technique for Correcting Both Incontinence and Cystocele: T.I.C.T.", Urogynaecologia International Journal (2001): pp. 133-140, vol. 15, No. 3.

Search Report PCT/EP 01/01/01977, dated Jan. 6, 2001.

* cited by examiner

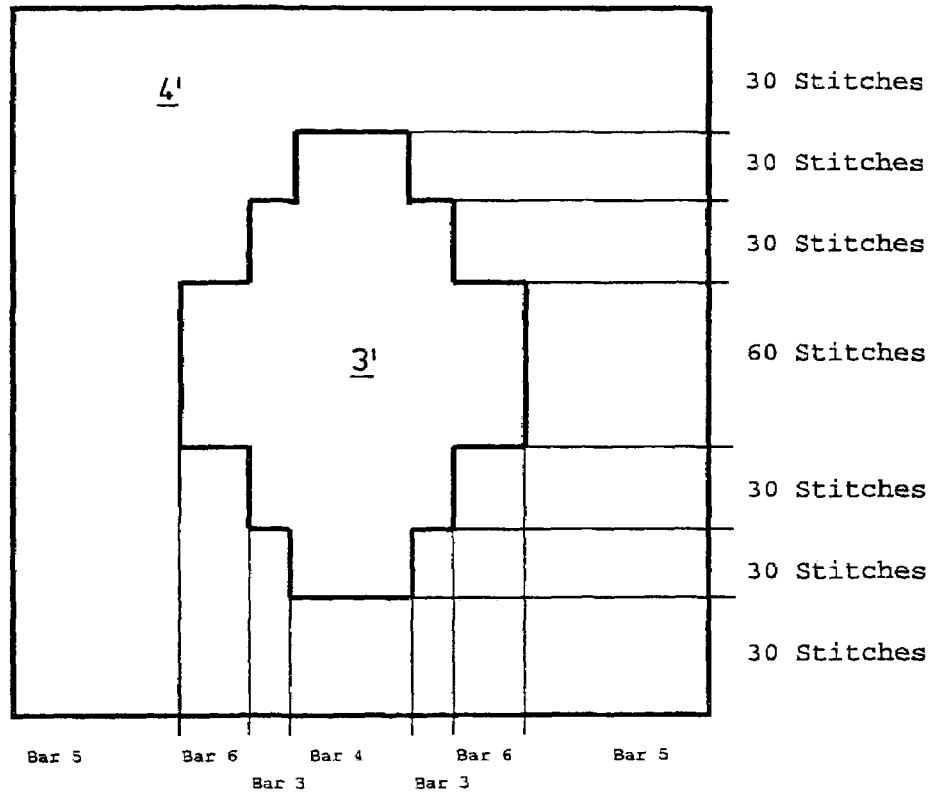

| Bar 3<br>4 Thread<br>guides | | | Bar 4<br>10 Thread<br>guides | | | Bar 5<br>12 Thread<br>guides | Bar 6<br>6 Thread<br>guides | | |
|---|---|---|---|---|---|---|---|---|---|
| 0 | 0 | 0 | 0 | 0 | 0 | 0 | 0 | 0 | 0 |
| $\frac{4}{2}$ | $\frac{4}{2}$ | $\frac{4}{2}$ | $\frac{4}{2}$ | $\frac{4}{2}$ | $\frac{4}{2}$ | $\frac{4}{2}$ | $\frac{4}{2}$ | $\frac{4}{2}$ | $\frac{4}{2}$ |
| $\frac{6}{2}$ | $\frac{4}{2}$ | $\frac{6}{2}$ | $\frac{6}{2}$ | $\frac{4}{2}$ | $\frac{6}{2}$ | $\frac{6}{2}$ | $\frac{6}{2}$ | $\frac{4}{2}$ | $\frac{6}{2}$ |
| $\frac{4}{(x10)}$ | $\frac{6}{2}$ | $\frac{4}{(x10)}$ | $\frac{4}{(x5)}$ | $\frac{6}{2}$ | $\frac{4}{(x5)}$ | $\frac{4}{(x40)}$ | $\frac{4}{(x15)}$ | $\frac{6}{2}$ | $\frac{4}{(x15)}$ |
| | $\frac{4}{2}$ | | | $\frac{4}{2}$ | | | | $\frac{4}{2}$ | |
| | $\frac{4}{(x12)}$ | | | $\frac{4}{(x18)}$ | | | | $\frac{4}{(x6)}$ | |

FIG. 3

50

IMPLANT

The invention relates to a surgical implant, the preferred versions of which can be used for treating inguinal hernias.

From WO 92/19162 an implant is known for closing an opening in a body wall caused by a hernia. The implant consists of an areal component, from the central area of which a type of plug projects. A further areal component is optionally attached to the free end of the plug. This implant can be folded and guided to the area of surgery with the help of a tube. There, the implant is pushed out of the tube so that the plug fills the opening to be closed while the areal component and where appropriate the optional additional areal component lie laterally against the tissue. Elastic stiffening structures can be provided in order that the implant automatically unfolds after it has been pushed out of the tube.

A further implant for repairing a hernia in a muscle wall is described in WO 92/13500. This implant contains an areal component from which a protruberance projects which can be closed with the help of a flap. The protruberance is introduced into the hernia defect and stability is achieved by filling the protruberance with a viscous liquid, which is prevented from leaking by the flap.

The previously known implants have a relatively large mass and thus form a relatively large foreign body in the patient, which is not advantageous for the healing process.

It is the object of the invention to provide an implant with a relatively small mass which can be designed as a safe implant for treating a hernia and can be used without difficulty.

This object is achieved by an implant having the features of claim 1. Advantageous designs of the invention result from the dependent claims.

The implant according to the invention has an areal basic structure made from a weft-knitted or warp-knitted fabric. The weft-knitted or warp-knitted fabric of the areal basic structure has a greater extendability in a central area of the implant than in the peripheral area of the implant; the difference in the extendabilities is preferably at least 20% in at least one direction. (The extendability of a sample is inversely proportional to the force necessary for achieving a pre-selected relative change in length of, e.g., 5%). This greater extendability is preferably achieved by arranging for the mass per surface unit area of the weft-knitted or warp-knitted fabric of the areal basic structure to be smaller in a central area of the implant than in the peripheral area of the implant. The smaller mass per unit area can be achieved by arranging for the mesh density of the weft-knitted or warp-knitted fabric of the areal basic structure to be smaller in a central area of the implant than in the peripheral area of the implant. The weft-knitted or warp-knitted fabric is preferably made in one piece (e.g. using a uniform yarn). Many possibilities are conceivable for the shape of the area of the basic structure with greater extendability; thus this area can be e.g. square, rectangular, cruciform, polygonal, round or also have other shapes.

Thus, the areal basic structure of the implant is more extendable and preferably lighter or less dense in a central area than in the peripheral area, but nevertheless has there a sufficient stability when the amount of material per surface unit is smaller. The term "central area" is to be broadly understood and is not limited to the geometric centre.

A particular advantage of the implant manifests itself when, in preferred versions, the basic structure in a central area of the implant (i.e. in an area with greater extendability of the basic structure) is deformed to produce a projection into the third dimension. The projection is preferably designed as a hollow protruberance and can be broadened mushroom-like in the area of its free end. Because of the greater extendability of the basic structure in the central area of the implant, the projection can be shaped without overstretching the material of the implant, which would lead to an undesired loss of strength. A comparable projection could not be immediately formed from a uniformly dense areal basic structure, say a conventional implant mesh; this would rather lead to an undesired wrinkling or to a local overstretching of the material until cracks formed and an associated undesired decrease in strength resulted.

The projection of the implant according to the invention is preferably dimensionally stabilized. This can be achieved, e.g., with the help of a heat treatment to which the implant is subjected after forming the projection. (The above-used term "extendability" relates to the basic structure, not to the finished projection, the material properties of which can be influenced by the shaping and stabilizing process.)

When the implant is provided for the treatment of a hernia, e.g. an inguinal hernia, the projection is introduced into the hernia defect while the areal basic structure is laid against the body wall structures in the largely flat peripheral area of the implant in the area surrounding the hernia and is optionally attached to it. As the basic structure is manufactured from a weft-knitted or warp-knitted fabric, it is flexible and the projection also has a sufficient flexibility even after a heat treatment conferring dimensional stability. During the healing process, tissue grows through the meshes of the weft-knitted or warp-knitted fabric. Apart from the flexibility of the implant, a relatively small mass also has a favourable effect.

In preferred versions, the implant according to the invention has a stiffening structure in the area of the free end of the projection. This stiffening structure can be annular or disc-like and can preferably be folded. It is advantageous if the stiffening structure is automatically expandable, from a folded state into an unfolded state, e.g. through the action of a spring or due to the elasticity behaviour of the material used for the stiffening structure.

The stiffening structure strengthens the projection. If the projection broadens mushroom-like in the area of its free end and is provided there with the stiffening structure, then a defect in a body tissue can be particularly reliably closed. This is because, in this case, the peripheral area of the basic structure of the implant lies against one side of the tissue while the projection is secured on the other side of the tissue by the mushroom-like broadening. If the stiffening structure automatically unfolds, the implant can be used in a particularly swift manner which treats the patient gently. To this end, a tube can be used as an auxiliary means, into which the implant is inserted while folded up. After the tube has been guided to the point of operation, the implant is pushed out of the tube e.g. with the help of a rod so that the projection can penetrate into the opening to be closed and the stiffening structure can unfold.

An advantageous version, the stiffening structure has an annular or disc-like support from the periphery of which several elastic arcs extend, which are distributed over the circumference. The elastic arcs preferably consist of thread material, e.g. polypropylene monofilament. Many designs are conceivable for the support. It can be flat, but also curved like a cap. It is preferably designed as an injection-moulded part, e.g. made from polypropylene, the elastic arcs mentioned being optionally fixed in their end-areas during the injection-moulding process.

In the light of the intended use, the implant according to the invention can consist completely of non-resorbable material, completely of resorbable material or of both resorbable and non-resorbable material. Multifilaments and monofilaments come into consideration for the weft-knitted or warp-knitted fabric of the basic structure. A preferred non-resorbable material is polypropylene, a preferred resorbable material is polyglactin 910 (a copolymer made from glycolide and L-lactide in the ratio 9:1). Other polymers and copolymers can also be used. A criterion for the choice of material is the intended use of the implant, on which e.g. the necessary flexibility and tensile strength and the necessary long-term behaviour in the body depend.

The implant according to the invention is described in more detail in the following by means of embodiments. The drawings show in FIG. 1 a threadline representation of a first version of the implant according to the invention, FIG. 2 a schematic representation of the thread guide distribution (upper part) and the pattern template (lower part) of the version according to FIG. 1, FIG. 3 a schematic representation of the thread guide distribution (upper part) and the pattern template (lower part) of a second version of the implant according to the invention, FIG. 4 a schematic representation of the thread guide distribution (upper part) and the pattern template (lower part) of a third version of the implant according to the invention, FIG. 5 in parts (a) to (d) schematic longitudinal sections through forms, with the help of which a projection is formed from a central area of the implant according to the invention, FIG. 6 in part (a) a side view and in part (b) a top view of a stiffening structure for stabilizing a projection formed on the implant according to the invention, FIG. 7 a schematic sectional representation of a version of the implant according to the invention with a projection formed thereat which is stabilized by the stiffening structure according to FIG. 6, the projection being inserted into a hernia defect, and FIG. 8 a loop representation of a weft-knitted product which is suitable for the central area of the basic structure of an implant according to the invention.

A threadline representation of a first version of an implant 1 is shown in FIG. 1 in a manner familiar to the person skilled in the art. The implant 1 has a basic structure 2 which consists of a warp-knitted fabric in the embodiment, namely crocheted galloon fabric. In a central area 3 of the basic structure 2, which is cruciform in the embodiment, the mass per surface unit is smaller than in the peripheral area 4 of the basic structure 2. In the embodiment, this difference is achieved by virtue of the fact that the number of partial picks laid in the pillar stitch of the warp-knitted fabric is smaller in the central area 3 than in the peripheral area 4, as is illustrated in FIG. 1. The warp-knitted fabric of the basic structure 2 is made in one piece in the embodiment. The peripheral area 4 of the basic structure 2 can extend further than shown in FIG. 1.

Figure 2:
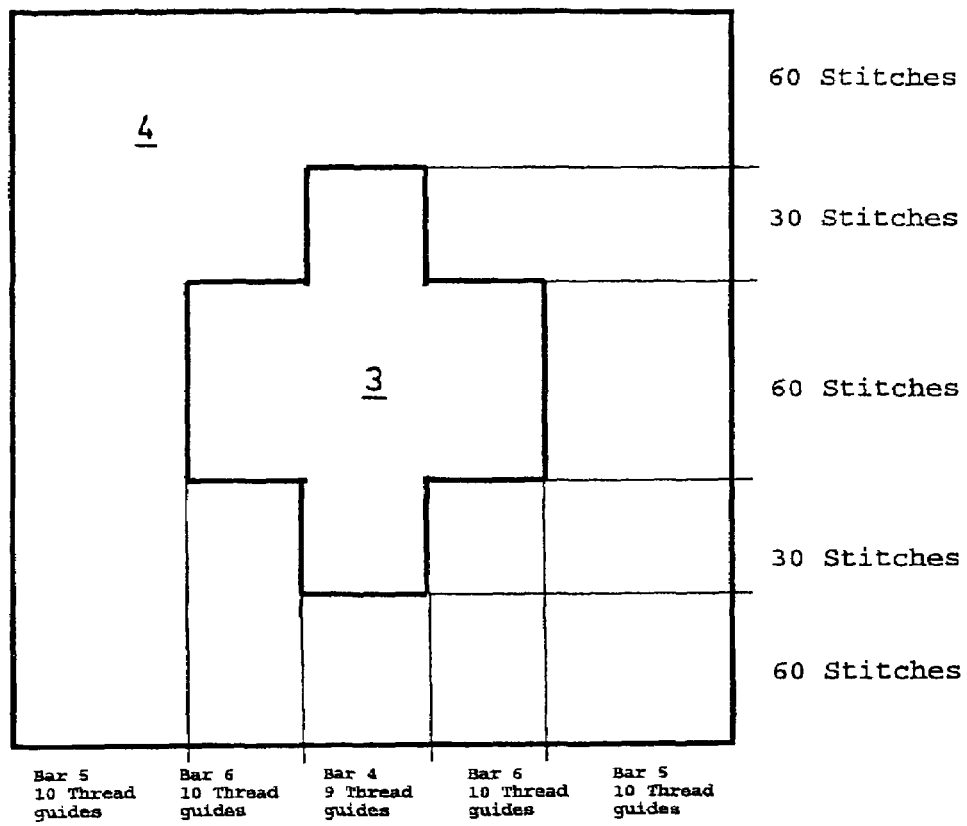

FIG. 2 shows the pattern template and the thread guide distribution for the embodiment according to FIG. 1 in a manner of representation known to the person skilled in the art. The implant 1 was manufactured as crocheted galloon fabric on a Müller, Frick (Switzerland) "Raschelina RD3MT3" type crochet galloon machine. Polypropylene threads of 60 den were worked in pillar stitch and polypropylene threads of 140 den in weft. The pattern wefts form the cruciform central area 3 of the implant. The course of the threads results from the pattern template and from the thread guide distribution.

FIG. 3 illustrates the pattern template and the thread guide distribution of a second version of the implant, where the central area is numbered 3' and the peripheral area 4'. By using additional thread guides, the resulting contour of the central area 3' is different from that in the version according to FIGS. 1 and 2. Manufacture took place on the same crochet galloon machine and with the same thread material as in the first version.

Figure 4:
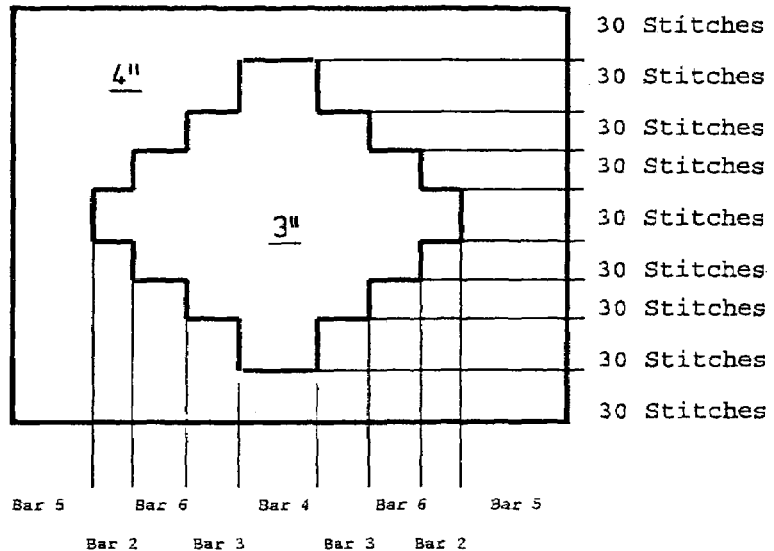

FIG. 4 shows the pattern template and the thread guide distribution for a third version of the implant, the central and peripheral areas of which are numbered 3" and 4", respectively. It becomes clear how, with an even greater number of thread guides, a contour of the central area 3" with an even greater number of corners can be achieved, so that the resulting contour here is almost that of a rhombus standing on its tip. The crochet galloon machine and the thread material of the first version were again used.

Many designs are conceivable for the shape of the central basic structure of the implant, thus apart from the cruciform and polygonal shapes already considered, also a rectangular or square shape, but also round shapes. The latter can be approximately achieved by polygonal shapes with a large number of corners. In the versions shown above, the areal basic structure of the implant has a smaller mass in the central area considered (which does not have to be arranged around the geometric centre) than in the peripheral area. In this way, the basic structure is more extendable in the central area. In principle, however, a greater extendability can also be achieved in the central area through differences in the type of knit or in the choice of material, even if the mass per surface unit is greater in the central area of the implant than in the peripheral area.

In the versions according to FIGS. 1 to 4, the areal basic structure is made in one piece. It is however also conceivable to manufacture the materials for the central and the peripheral area separately and to insert (e.g. by embroidering, sewing or gluing) a piece of material for the central area into a recess which is formed in a piece of material for the peripheral area.

In the following table 1, the material and the mesh structure are shown for various warp-knitted fabrics, which are designated by "fabric 1" to "fabric 10".

TABLE 1

Material and mesh structure of various warp-knitted fabrics.

| Fabric | Material and mesh structure |
|---|---|
| 1 | 3 mil "Pronova" monofilament in warp and weft, hexagonal structure |
| 2 | 3 mil "Pronova" monofilament in warp and weft, rectangular structure |
| 3 | 3 mil "Pronova" monofilament in warp and weft, hexagonal structure with striped tie-in |
| 4 | 3 mil "Pronova" monofilament in warp and weft, rectangular structure |
| 5 | 3 mil "Pronova" monofilament in warp and weft, hexagonal structure |
| 6 | 60 den polypropylene multifilament in warp and 2 × 70 den polypropylene multifilament in weft, hexagonal structure |
| 7 | 60 den polypropylene multifilament in warp and 2 × 70 den polypropylene multifilament in weft, hexagonal structure with striped tie-in |

TABLE 1-continued

Material and mesh structure of various warp-knitted fabrics.

| Fabric | Material and mesh structure |
|---|---|
| 8 | 60 den polypropylene multifilament in warp and 2 × 70 den polypropylene multifilament in weft, rectangular structure |
| 9 | 60 den polypropylene multifilament in warp and 2 × 70 den polypropylene multifilament in weft, honeycomb structure |
| 10 | 60 den polypropylene multifilament in warp and 2 × 70 den polypropylene multifilament in weft, hexagonal structure |

1 mil = 0.0254 mm
"Pronova" is a trademark for poly(vinylidenefluoride-co-hexa-fluoropropylene) used by Ethicon GmbH.

The force necessary for a 5% extension in different directions of the warp-knitted fabrics in Table 1 is shown in Table 2. Furthermore, Table 2 shows the thickness and the mass per unit area of these warp-knitted fabrics and additionally the comparison data for two conventional implant meshes, which are designated A and B in the Table. Mesh A (marketed by Ethicon GmbH under the name "Prolene Netz") is prepared from a polypropylene monofilament with a thickness of 6 mil. Mesh B also consists of polypropylene monofilaments and is marketed by Atrium Medical Corporation, 5 Wentworth Drive, Hudson, N.H. 03051, U.S.A., under the name "atrium POLYPROPYLENE MESH".

The force necessary for a 5% extension was determined with the help of a "ZWICKI 1120" test apparatus from Zwick GmbH, Ulm, on samples 60 mm wide and 100 mm long. The gauge length of the respective sample measured in longitudinal direction was 25 mm. The sample width extending in cross-direction corresponded to the 60 mm width of the rubber-coated jaws of the test apparatus. An initial force of 0.1 Newtons was built up at a speed of 2 mm/min. The distance between the jaws was then increased at a test speed of 20 mm/min until a 5% sample extension was achieved. The force occurring in this process was measured and is stated in Table 2 for various directions of the knitted structure of the individual samples.

TABLE 2

Properties of the warp-knitted fabrics from Table 1 and of two previously known implant meshes.

| Fabric | Longitudinal [N] | Transverse [N] | Diagonal [N] | Thickness [mm] | Mass per unit area [g/m²] |
|---|---|---|---|---|---|
| 1 | 16.46 | 8.71 | 9.26 | 0.29 | 39.85 |
| 2 | 25.66 | 19.4 | 18.79 | 0.36 | 41.40 |
| 3 | 20.45 | 7.37 | 12.21 | 0.30 | 44.40 |
| 4 | 38.19 | 5.44 | 17.39 | 0.30 | 38.75 |
| 5 | 1.35 | 0.89 | 3.09 | 0.26 | 29.61 |
| 6 | 24.82 | 3.28 | 12.11 | 0.37 | 42.01 |
| 7 | 47.18 | 13.33 | 21.76 | 0.40 | 37.29 |
| 8 | 47.77 | 1.41 | 12.80 | 0.40 | 32.53 |
| 9 | 0.99 | 3.55 | 5.32 | 0.29 | 22.03 |
| 10 | 41.62 | 1.59 | 4.41 | 0.25 | 17.58 |
| A | 125 | <0.5 | 152.2 | 0.6 | 95.2 |
| B | 130 | 50 | 92.9 | 0.46 | 92 |

The structure of the warp-knitted fabric 5 is the same as the knitted structure of the central area 3 of the implant 1 according to FIGS. 1 and 2. Table 2 shows that the extendability of the warp-knitted fabric 5 is particularly high. The warp-knitted fabric 9 also has a great extendability. The structures of the warp-knitted fabrics 5 and 9 are therefore particularly suitable for the central area of an implant of the type considered here. The structures of the other warp-knitted fabrics, which have a smaller extendability and generally also a higher mass per unit area, come into consideration in particular for the peripheral area of such an implant. For the peripheral area, however, structures are also conceivable as with the conventional meshes, the extendability of which is generally even smaller.

Figure 7:
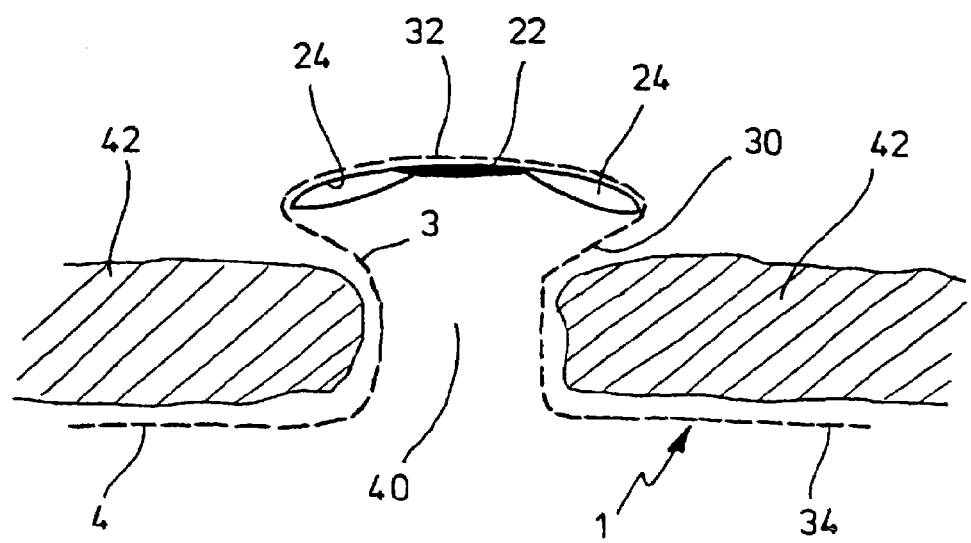

In preferred versions of the implant, the basic structure in the particularly extendable central area is deformed to produce a projection into the third dimension. FIG. 7 shows a schematic section through a completely shaped implant 1; various designs for forms for the development of the projection, however, will be explained first with reference to FIG. 5.

Figure 5:
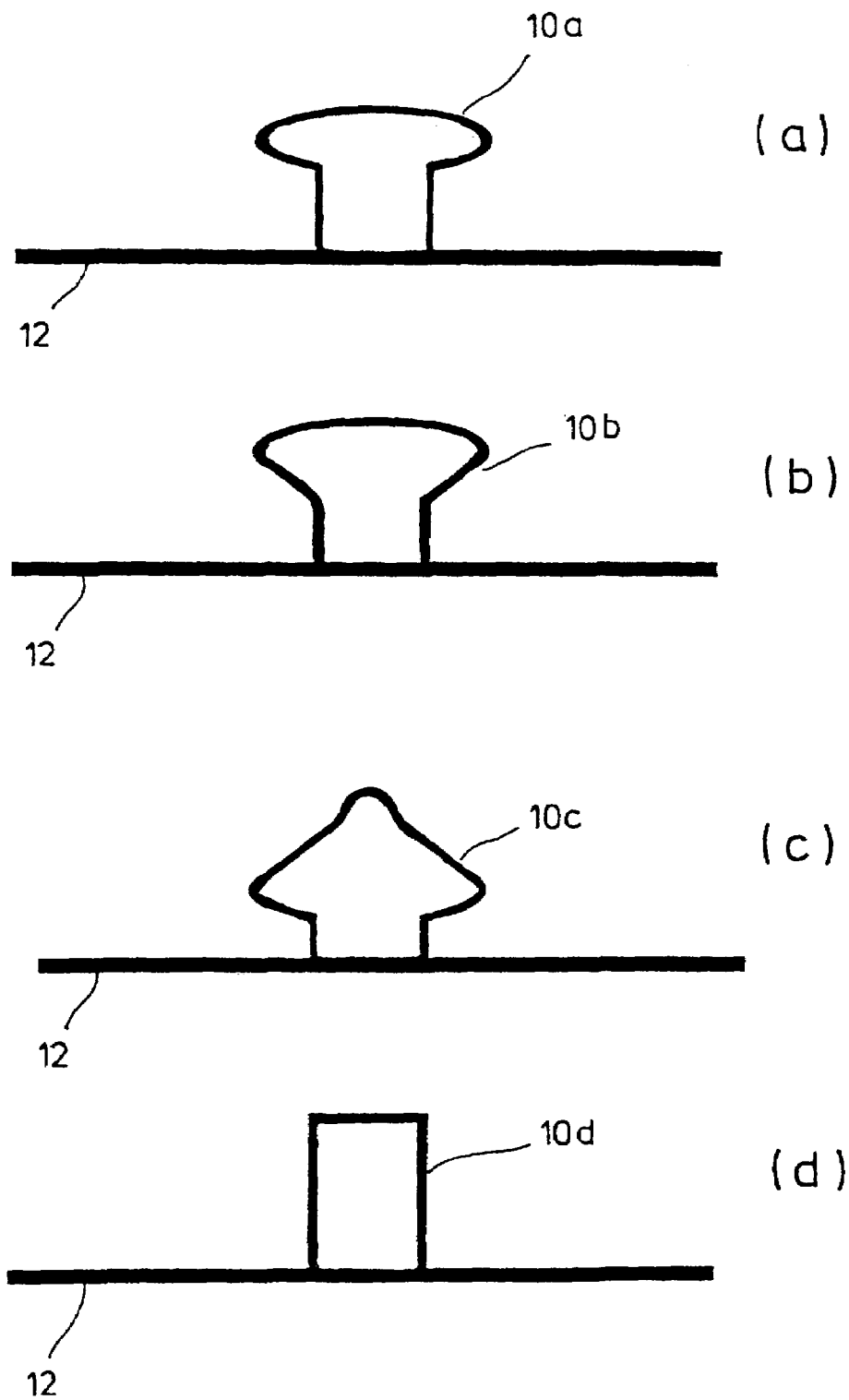

FIG. 5 shows in parts (a) to (d) four examples of such forms in schematic longitudinal section. In each case a rotationally symmetrical form 10a, 10b, 10c or 10d is attached to a base plate 12. The respective forms 10a, 10b, 10c or 10d and the base plate 12 are preferably made from metal.

In order to deform the basic structure of an implant, which is areal after its manufacture, into the third dimension, the basic structure is firstly heated to a temperature which still lies clearly (e.g. at least 10 K) below the (lowest) melting point of the material of which the basic structure consists. The basic structure is then pressed against one of the forms 10a to 10d (or else a differently designed form) in a central area, while the peripheral area of the basic structure lies against the base plate 12.

At the increased temperature, the material of the basic structure softens so that a projection in the shape of a hollow protuberance is developed in the basic structure by the form 10a, 10b, 10c or 10d, without the material of the basic structure being overstressed or even tearing as a result of the occurring extensions. During the shaping it proves favourable that the weft-knitted or warp-knitted fabric, in the zone which is extended by the form 10a, 10b, 10c or 10d, is be designed beforehand for greater extendability.

A heat treatment is preferably carried out on the implant after the projection has been formed, in order to stabilize the projection. If the implant (as in the embodiments) is made from polypropylene, then a thermal treatment in the oven at 150° C. for 2 hours is particularly suitable.

After the projection has been formed and the thermal treatment has ended, the implant maintains its shape with the three-dimensional projection and is flexible both in the peripheral area and in the area of the projection.

Figure 6:
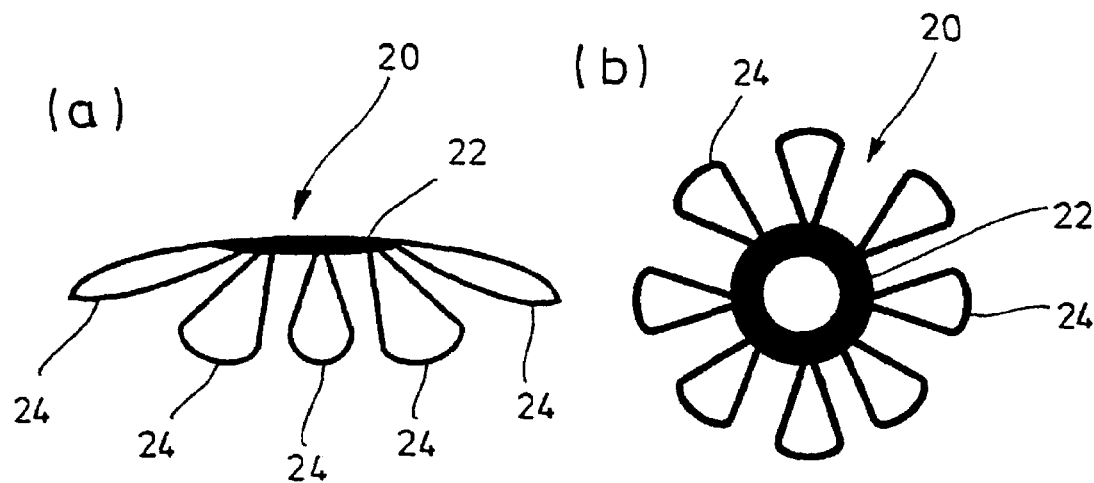

In FIG. 6 an example is shown of a stiffening structure 20 with the help of which the projection can be stabilized in the area of its free end, as is explained in more detail below with the help of FIG. 7. In the embodiment, the stiffening structure 20 includes an annular support 22, which is manufactured as an injection-moulding part made from polypropylene. During the injection-moulding process, elastic arcs 24 are cast into the edge area of the support 22, which in the embodiment are made from polypropylene monofilament. The arcs 24, eight in total, are regularly distributed over the circumference of the support 22, see FIG. 6 (b). The support 22 is slightly curved downwards in the manner of a cap so that the arcs 24 also point somewhat downwards in the representation according to FIG. 6 (a).

The stiffening structure 20 can be folded up or collapsed by pressing the flexible arcs 24 onto the centre of the support 22. If the arcs 24 are released or freed again, they automatically extend to their original shape (or at least largely to their original shape) so that the stiffening structure 20 again adopts the unfolded state represented in FIG. 6.

FIG. 7 illustrates an implant 1 with the basic structure according to FIGS. 1 and 2, where a projection 30 is formed in the central area 3 in the way described above. The warp-knitted fabric has a physiologically acceptable pore size in the area of the projection 30. To form the projection 30, the mushroom-like form 10b was used. The projection 30 is thus broadened mushroom-like in the area of its free end 32. In this area, the stiffening structure 20 described using FIG. 6 is inserted into the projection 30. The peripheral area 4 of the basic structure forms the largely flat edge area 34 of the implant 1.

FIG. 7 shows how the implant 1 is inserted into a hernia defect 40 which lies between tissue structures 42. Other tissue structures, such as skin or peritoneum, are not included in FIG. 7. The mushroom-like broadening of the projection 30, which is stabilized by the stiffening structure 20, preferably comes to rest between the tissue structures 42 and the peritoneum. In order to insert the implant 1 into the hernia defect 40, the implant 1 can be folded and inserted into a tube the outer diameter of which is roughly as large as the hernia defect 40. With the help of this tube, the implant 1 can be guided through the hernia defect 40. When the implant 1 is pushed out of the tube e.g. with the help of a rod, the stiffening structure 20 automatically unfolds and in the process gives the projection 30 the shape represented in FIG. 7.

Figure 8:
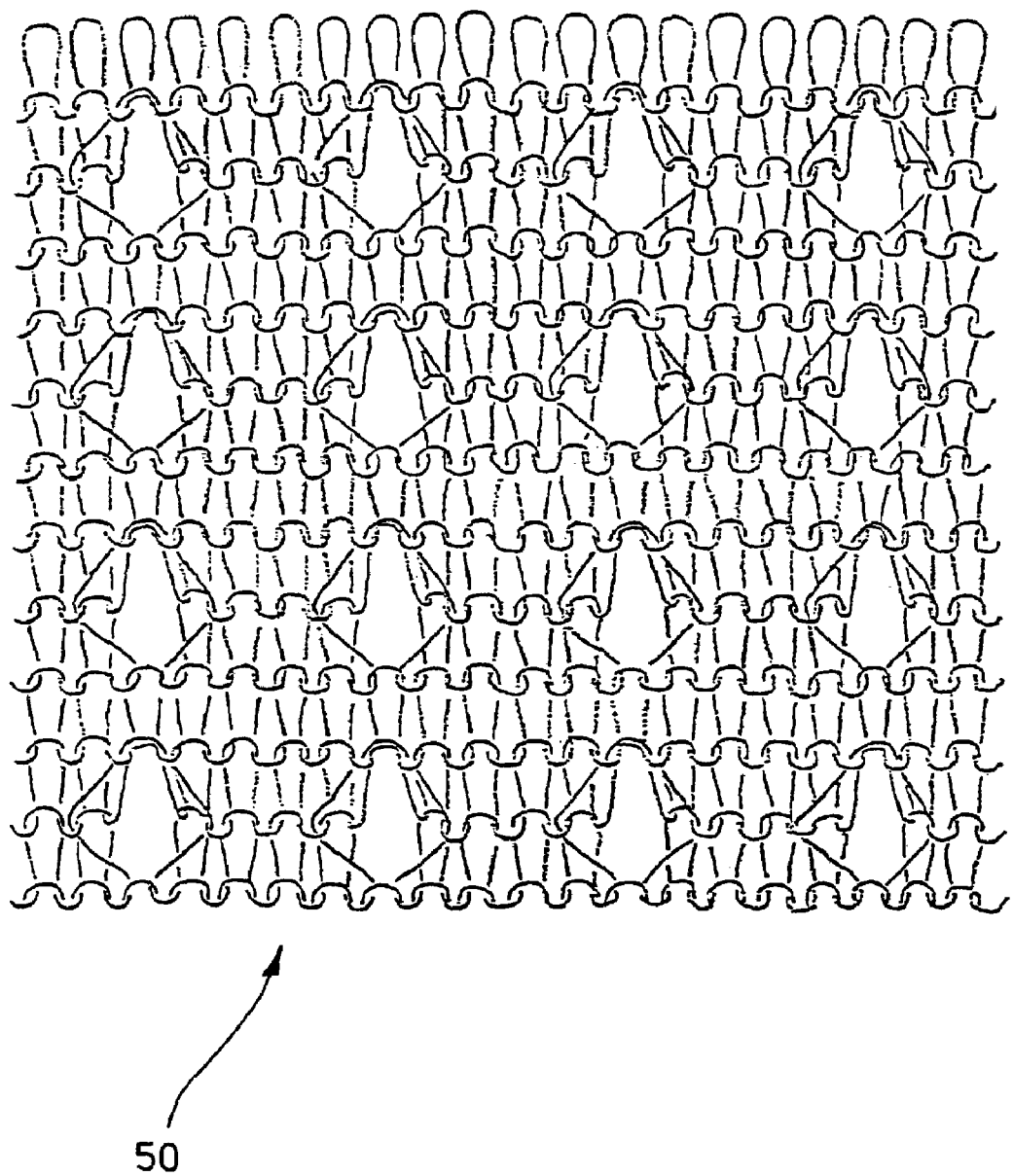

In the versions described up to now, the basic structure of the implant is warp-knitted. Weft-knitted fabrics can also be used, however. FIG. 8 shows the mesh representation of a weft-knitted fabric which is suitable for the central area of an implant. This weft-knitted fabric is a combined single-thread knitted fabric 50, which has thread loops of differing sizes. In the embodiment, the material used is polypropylene (60 den for the pillar stitch and 140 den for the weft).

The invention claimed is:

1. An implant, comprising a central area deformed to produce a broadened mushroom-like projection or a projection in the form of a hollow protuberance, the projection having a free end and a stiffening structure at the free end, the implant further comprising a peripheral area, wherein the mass per unit area of the central area is less than in the peripheral area.

2. The implant according to claim 1, wherein the projection is the hollow protuberance.

3. The implant according to claim 1, wherein the projection is dimensionally stabilized.

4. The implant according to claim 3, wherein the stiffening structure is annular or disc-like.

5. The implant according to claim 3, wherein the stiffening structure can be folded.

6. The implant according to claim 5, wherein the stiffening structure is expandable automatically from a folded state into an unfolded state.

7. The implant according to claim 6, wherein the stiffening structure has an annular or disc-like support from the periphery of which several elastic arcs extend, distributed over the circumference.

8. The implant according to claim 7, wherein the elastic arcs consist of thread material.

9. The implant according to claim 1, wherein the shape of the central area is selected from the group consisting of a square, rectangular, cruciform, polygonal or circle.

* * * * *